United States Patent [19]

Fischer

[11] Patent Number: Plant 5,535

[45] Date of Patent: Aug. 13, 1985

[54] AFRICAN VIOLET PLANT NAMED CINDARELLA

[75] Inventor: Arnold Fischer, Hanover, Fed. Rep. of Germany

[73] Assignee: Pan American Plant Company, Parrish, Fla.

[21] Appl. No.: 539,804

[22] Filed: Oct. 7, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet named Cindarella and particularly characterized by its bright pink flower color, compact rosette habit, with the flowers carried on erect peduncles, floriferous habit, and its medium green and slightly ruffled foliage.

1 Drawing Figure

The present invention comprises a new and distinct cultivar of African violet plant, botanically known as *Saintpaulia ionantha,* and hereinafter referred to by the cultivar name Cindarella.

The new cultivar as referred to during the breeding and selection process by the designation V6-8-2P, and is a product of a planned breeding program. The basic objective of the breeding program was to create a new African violet cultivar having numerous large bright pink, slightly ruffled flowers standing erect over medium green, slightly ruffled foliage.

The new cultivar was originated from a cross made in a controlled breeding program in Hannover, Germany. The male and female parents are unknown at this time.

Cindarella was discovered and selected by Arnold Fischer as a flowering plant within the progeny of the stated cross in a controlled environment in Hannover, Germany. Asexual reproduction of the new cultivar by leaf cuttings, as performed by Arnold Fischer at West Chicago, Ill. and Parrish, Fla., has demonstrated that the combination of characteristics as herein disclosed for the new cultivar are firmly fixed and retained through successive generations of asexual reproduction.

Cindarella has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Cindarella which in combination distinguish this African violet as a new and distinct cultivar.

1. Bright pink flower color, petals slightly ruffled.
2. Compact rosette habit, with flowers borne on very erect peduncles.
3. Suitable for production in 10 cm. pots, flowering in 10 to 12 weeks depending upon growing conditions.
4. Floriferous, with flowers continuing to open for weeks after onset of flowering.
5. Medium green foliage, pubescent and slightly ruffled with a crenate margin.

The new cultivar is most similar to New Jersey, disclosed in U.S. Plant Pat. No. 4,214. Cindarella is principally distinguished from New Jersey by its darker pink flower color with less of a tendency to fade, and by its ruffled foliage.

The accompanying photograhic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under 5000 ft. candles of natural light at approximately 11:00 A.M. in Parrish, Fla.

Botanical classification: *Saintpaulia ionantha,* Ramat. cv. Cindarella.

Parentage:

*Male parent.*—Unknown.

*Female parent.*—Unknown.

Propagation: The new cultivar holds its distinguishing characteristics through successive propagations by leaf cuttings.

Plant: From 4 cm. to 9 cm. tall when grown in pots, and approximately 23 cm. in diameter when fully grown. The growth rate is vigorous, and the general shape of the fully grown plant is round.

*Leaves.*—Quantity: Abundant. Shape: Cordate with crenate margin. Diameter: 5–8 cm. Texture: Pubescent/glossy. Ribs and veins: Pinnate. Color (Upperside): 147A. Color (Underside): 147D in most interveinal areas; veins 185B, and 185B mixed with 147D in some areas. Petioles: 4–10 cm. in length.

*Flowers.*—Buds: Size: Up to 1 cm. in diameter and length. Shape: Round. Rate of opening: Normal. Color: Ranging from 75A to 75D. Sepals: Shape: Lanceolate. Color: 183B with showing of 147D. Phyllaries: Two; lanceolate. Color: 147B adaxial. Calyx: Shape: Funnel. Size: 10–12 mm. in diameter. Aspect: Hairy. Peduncle: Length: 4–7 cm. Character: Erect, rigid. Color: 181B with showing of 147D. Individual Flowers: Number of petals: 5 to 7. Size: 25–40 mm. diameter and 10–15 mm. deep. Shape: Cup shaped when bloom first opens, becoming flat as bloom matures. Color: Upperside: Outer edges 75B, shading into 73A in the center. Underside: 75C. Flowers fade slightly as they age. Color varies with amount of light, fertilizer, temperature and other growing conditions. Borne: Cymose clusters formed on upright peduncles 4 to 7 cm. in length. Flowering Habit: Flowers profusely and intermittently year round with blooms lasting 2–3 weeks after which petals dry up and turn brown but do not drop; finishes in 10–12 weeks when a 2½" plantlet is placed in a 10 cm. pot.

*Reproductive organs.*—Stamens: Borne singly around the ovary; anthers basifixed, 2–5 in number. Anthers: 3 mm.×3 mm. in size, yellow color. Filaments: 2–3 mm. in length, pinkish-yellow. Pollen Color: Yellow. Pistels: Number: One. Styles: One, 6–8 mm. long, color 71D color. Stigma: Split, white. Ovaries: Superior. Roots: Fine, fiberous. Disease resistance: No diseases noted to date.

General observations: Cindarella is a new and unique variety with abundant bright pink ruffled flowers which stand very erect above slightly ruffled, medium green foliage. The flowers are zygomorphic rotate singles with 5 petals, with an occasional semi-double flower showing up. This plant may be finished in 10–12 weeks from a 2¼" plantlet in a controlled environment.

I claim:

1. A new and distinct cultivar of African violet named Cindarella, as described and illustrated, and particularly characterized by its bright pink flower color; compact rosette habit, with the flowers carried on erect peduncles; floriferous habit, and its medium green and slightly ruffled foliage.

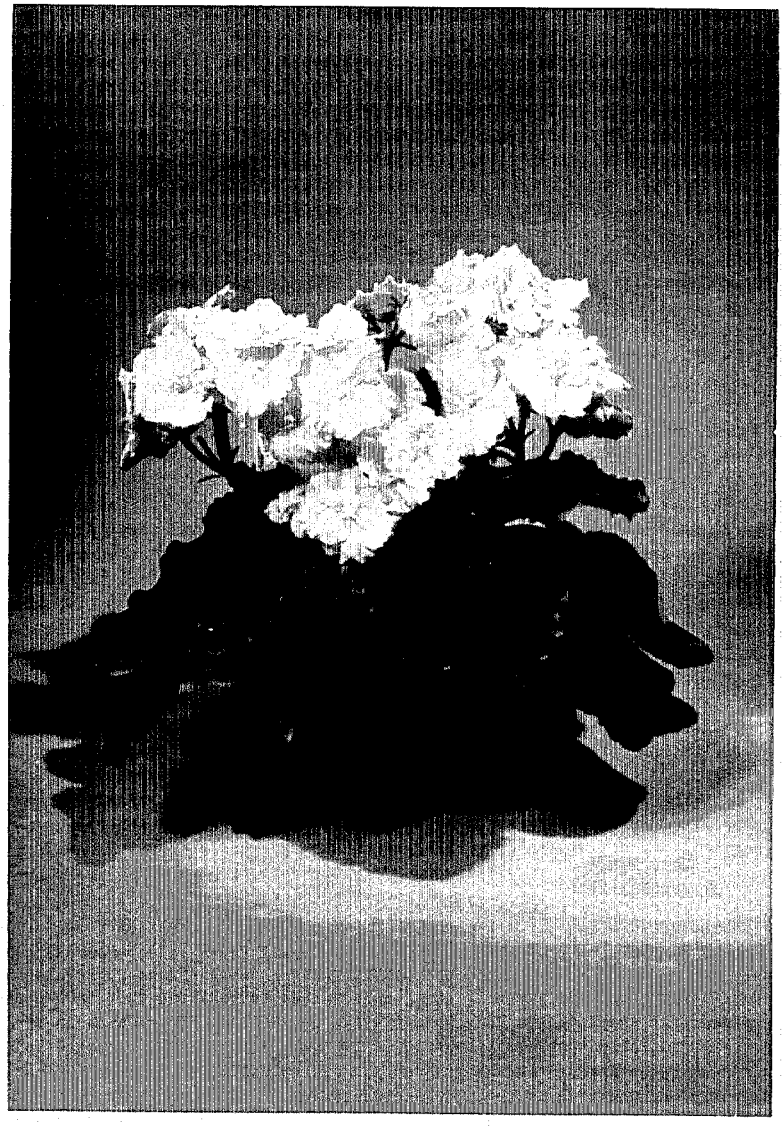

* * * * *